United States Patent
Liachko et al.

(10) Patent No.: US 11,753,637 B2
(45) Date of Patent: Sep. 12, 2023

(54) METHOD FOR THE CLUSTERING OF DNA SEQUENCES

(71) Applicant: Phase Genomics Inc., Seattle, WA (US)

(72) Inventors: Ivan Liachko, Seattle, WA (US); Shawn Thomas Sullivan, Seattle, WA (US); Kyle Langford, Seattle, WA (US); Stephen M. Eacker, Seattle, WA (US)

(73) Assignee: Phase Genomics Inc., Seattle, WA (US)

( * ) Notice: Subject to any disclaimer, the term of this patent is extended or adjusted under 35 U.S.C. 154(b) by 167 days.

(21) Appl. No.: 16/625,203

(22) PCT Filed: Jun. 26, 2018

(86) PCT No.: PCT/US2018/039454
§ 371 (c)(1),
(2) Date: Dec. 20, 2019

(87) PCT Pub. No.: WO2019/005763
PCT Pub. Date: Jan. 3, 2019

(65) Prior Publication Data
US 2020/0140943 A1 May 7, 2020

Related U.S. Application Data

(60) Provisional application No. 62/524,815, filed on Jun. 26, 2017.

(51) Int. Cl.
*C40B 30/04* (2006.01)
*C12N 15/10* (2006.01)
(Continued)

(52) U.S. Cl.
CPC ....... *C12N 15/1093* (2013.01); *C12Q 1/6806* (2013.01); *C12Q 1/6874* (2013.01)

(58) Field of Classification Search
CPC ................ C12Q 1/6874; C12Q 1/6806; C12N 15/1093; G01N 1/30
See application file for complete search history.

(56) References Cited

U.S. PATENT DOCUMENTS

| 5,476,930 A | 12/1995 | Letsinger et al. |
| 5,780,613 A | 7/1998 | Letsinger et al. |

(Continued)

FOREIGN PATENT DOCUMENTS

| CN | 103981263 A | 8/2014 |
| JP | 2016-537029 A | 12/2016 |

(Continued)

OTHER PUBLICATIONS

Hakim et al. "Snapshot: Chromosome Conformation Capture" Cell 148:5, Mar. 2012, pp. 1068-1068.e2 on three sheets; DOI 10.1016/j.cell.2012.02.019 (Year: 2012).*

(Continued)

*Primary Examiner* — Christian C Boesen
(74) *Attorney, Agent, or Firm* — COOLEY LLP

(57) ABSTRACT

Methods and compositions are provided for performing an in vivo proximity-ligation in combination with DNA capture technology to cross-link physically adjacent DNA sequences within a mixed population of cells and isolate cross-linked DNA junctions where at least one DNA sequence of interest is present.

23 Claims, 2 Drawing Sheets

Specification includes a Sequence Listing.

(51) Int. Cl.
*C12Q 1/6806* (2018.01)
*C12Q 1/6874* (2018.01)

(56) References Cited

U.S. PATENT DOCUMENTS

| | | | |
|---|---|---|---|
| 2009/0047675 A1 | 2/2009 | Roberts et al. | |
| 2009/0107913 A1* | 4/2009 | Johnson | 210/604 |
| 2011/0045462 A1* | 2/2011 | Fu et al. | 435/6 |
| 2013/0096009 A1* | 4/2013 | Dekker et al. | C12Q 1/6837 |
| 2016/0239602 A1* | 8/2016 | Shendure et al. | G06F 19/22 |
| 2016/0289738 A1 | 10/2016 | Grosveld et al. | |
| 2017/0314014 A1* | 11/2017 | Green et al. | C12N 15/1065 |

FOREIGN PATENT DOCUMENTS

| | | |
|---|---|---|
| WO | WO 2015/071748 A1 | 5/2015 |
| WO | WO 2017/068379 A1 | 4/2017 |

OTHER PUBLICATIONS

Mascher et al. "A chromosome conformation capture ordered sequence of the barley genome" Nature 544, pp. 427-433 (2017) with Methods and Supplemental Information totaling 22 pages at doi:10.1038/nature22043; published: Apr. 26, 2017 (Year: 2017).*

Fraser et al. "An overview of genome organization and how we got there: from FISH to Hi-C" Microbiol Mol Biol Rev (Jul. 29, 2015) 79(3):347-372; doi:10.1128/MMBR.00006-15 (Year: 2015).*

Utter et al. "Beyond the Chromosome: The Prevalence of Unique Extra-Chromosomal Bacteriophages with Integrated Virulence Genes in Pathogenic *Staphylococcus aureus*." (2014) PLOS One 9(6): e100502. doi:10.1371/journal.pone.0100502 (Year: 2014).*

Młynarczyk et al. "The genome of *Staphylococcus aureus*: a review." Zentralbl Bakteriol. May 1998;287(4):277-314. doi: 10.1016/s0934-8840(98)80165-5. (Year: 1998).*

International Search Report and Written Opinion of the International Searching Authority for International Application No. PCT/US2018/039454 dated Sep. 18, 2018, pp. 1-18.

Extended European Search Report for European Application No. 18822702.9 dated Mar. 22, 2021.

Martin et al., "Capture Hi-C reveals novel candidate genes and complex long-range interactions with related autoimmune risk loci," Nature Communications, 2015, 6:10069, 7 pages.

Mifsud et al., "Mapping long-range promoter contacts in human cells with high-resolution capture Hi-C," Nature Genetics, Jun. 2015, vol. 47, No. 6, pp. 598-606.

International Preliminary Report on Patentability for International Application No. PCT/US2018/039454 dated Dec. 31, 2019, 15 pages.

* cited by examiner

FIG. 2A
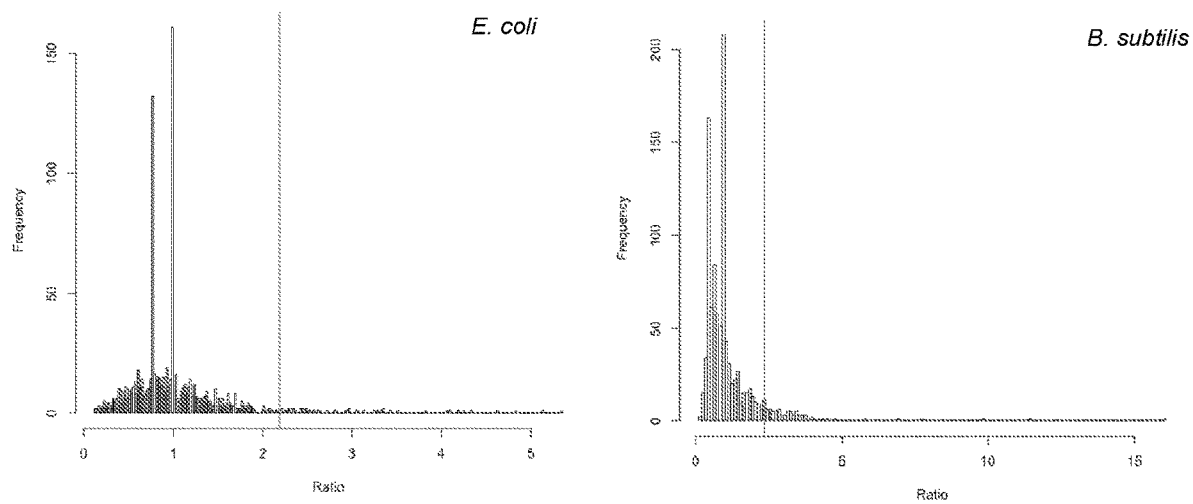
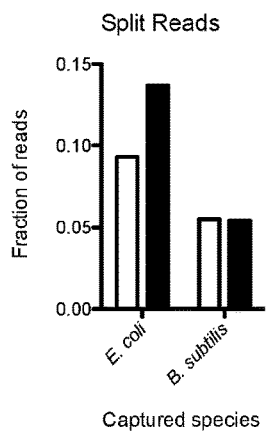
FIG. 2B
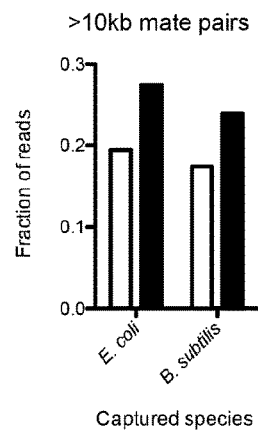
FIG. 2C
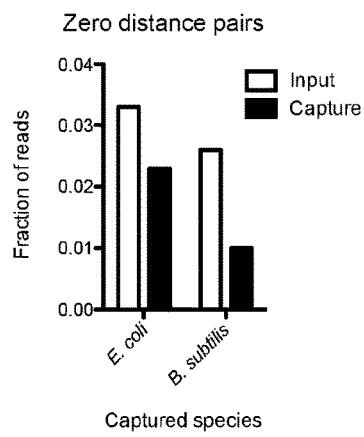
FIG. 2D

```
SEQUENCE LISTING

<160> NUMBER OF SEQ ID NOS: 2

<210> SEQ ID NO 1
<211> LENGTH: 139
<212> TYPE: DNA
<213> ORGANISM: Artificial Sequence
<220> FEATURE:
<223> OTHER INFORMATION: Bacillus subtilis Capture Probe

<400> SEQUENCE: 1
tgattttcct caaaatatgc tcaatccaaa atatactttt gatactttg tcatcggatc      60 tggaaaccga tttgcacatg ctgcttccct cgcagtagcg gaagcgcccg cgaaagctta     120 caaccctta tttatctat                                                  139

<210> SEQ ID NO 2
<211> LENGTH: 140
<212> TYPE: DNA
<213> ORGANISM: Artificial Sequence
<220> FEATURE:
<223> OTHER INFORMATION: Escherichia coli Capture Probe

<400> SEQUENCE: 2
taatctgcgg aggcgtcagt ttccgcgcct catggatcaa ctgctgggaa ttgtctaaca     60
gctccggcag cgtatagcgc gtggtggtca acgggctttg gtaatcaagc gttttcgcag    120
gtgaaataag aatcagcata                                                140
```

METHOD FOR THE CLUSTERING OF DNA SEQUENCES

RELATED APPLICATIONS

This application is a national phase of International PCT Application No. PCT/US2018/039454, filed Jun. 26, 2018, which claims the benefit of priority to U.S. Provisional Application No. 62/524,815 filed Jun. 26, 2017, each of which is hereby incorporated by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is PHGE_001_01WO_SeqList_ST25.txt. The text file is ≈1 KB, was created on Jun. 26, 2018, and is being submitted electronically via EFS-Web.

BACKGROUND OF THE INVENTION

Currently, for pairs of DNA sequences that are far away in the genome or on different pieces of DNA inside a cell (such as on different chromosomes or on plasmids) it can be very difficult to tell by shotgun sequencing which two DNAs originated in the same cell. This can make very difficult to track antimicrobial resistance which can be transmitted by plasmids and other mobile elements. Normally, the cells of interest have to be clonally purified through culturing, and then sequenced individually (during this culturing step, the sequences of interest can be lost).

The present invention would address these needs and others by allowing a rapid method (without culturing) to test for which gene/sequence of interest is present in which strain background even if the two sequences are not on the same chromosome.

SUMMARY OF THE INVENTION

In one aspect, provided herein is a method that combines an in vivo proximity-ligation method (chromosome conformation capture, 3c) with DNA capture technology (ex. exome capture, capture hi-c, etc.) to crosslink physically adjacent DNA sequences within a mixed population of cells (such as, for example, an infection or microbiome sample or a mixed cell population from a tumor) and isolate cross-linked DNA junctions where at least one DNA sequence of interest (such as an antibiotic resistant gene or an oncogenic allele) is present. Once the cross-linked junctions containing a sequence of interest are purified, the remaining sequences attached to the sequence of interest are analyzed or determined. Analysis or determination of the sequences attached or associated with the sequence of interest can entail labeling of said sequence and hybridization to a microarray that is designed to query for specific other sequences and/or sequencing said sequences using, for example, next generation sequencing (NGS).

The end product of the methods and compositions provided herein can be the ability to select a sequence of interest and determine one or more of the other sequences present in the same cell as the sequence of interest.

In one aspect, provided herein is a method for determining a presence of one or more nucleic acids in a cell comprising a target nucleic acid, the method comprising: generating proximity junctions between one or more nucleic acids and a target nucleic acid in a cell, wherein the cell is present in a sample comprising a mixed cell population; capturing the proximity junctions between the one or more nucleic acids and the target nucleic acid, wherein the capturing comprises hybridizing the proximity junctions with an oligonucleotide comprising sequence complementary to the target nucleic acid; and analyzing the one or more nucleic acids in the proximity junctions hybridized to the oligonucleotide comprising sequence complementary to the target nucleic acid, thereby determining the presence of the one or more nucleic acids in the cell comprising the target nucleic acid. In some cases, the generation of the proximity junctions between one or more nucleic acids and the target nucleic acid comprises: i.) incubating the sample comprising the cell with a cross-linking agent, wherein the cross-linking agent cross-links proteins and the one or more nucleic acids with the target nucleic acid in the cell, thereby generating a complex between the one or more nucleic acids and the target nucleic acid; ii.) lysing the cell in a lysing buffer comprising a combination of one or more anionic detergents and one or more non-ionic detergents; iii.) digesting the nucleic acid within the complex between the one or more nucleic acids and the target nucleic acid, thereby generating free nucleic acid ends; iv.) ligating the digested nucleic acid; and v.) releasing the one or more proximity junctions from the cross-linked protein, thereby generating the proximity junctions between the one or more nucleic acids and the target nucleic acid. In some cases, the cross-linking reagent comprises formaldehyde. In some cases, the method further comprises the step of incubating the complex with a cross-linking quencher. In some cases, the cross-linking quencher is glycine. In some cases, the endonuclease is a restriction endonuclease. In some cases, the endonuclease is DNase. In some cases, the endonuclease is MNase. In some cases, the releasing comprises reversing cross-linking by treating the cross-linked proteins with an agent selected from protease, heat or a combination thereof. In some cases, the releasing comprises fragmenting the complex. In some cases, the oligonucleotide comprising sequence complementary to the target nucleic acid further comprises a moiety attached to a 5' end. In some cases, the moiety is biotin. In some cases, the oligonucleotide comprising sequence complementary to the target nucleic acid is bound to a solid substrate. In some cases, the solid substrate is selected from a bead, a well in a multi-well plate or surface of a slide. In some cases, the bead is a magnetic bead. In some cases, the method further comprises labeling the free nucleic ends with biotin prior to step v.), whereby the proximity junctions generated following step v.) are biotin labeled. In some cases, the proximity junctions that are biotin labeled are subjected to a purification step prior to capturing the proximity junctions, wherein the purification step comprises binding biotin with avidin or streptavidin attached to a solid substrate. In some cases, the capturing further comprises enriching the target nucleic acid, wherein the enriching comprises performing polymerase chain reaction (PCR) by adding a set of primers and PCR reagents to the proximity junctions hybridized with the oligonucleotide comprising sequence complementary to the target nucleic acid, wherein each primer in the set of primers comprises sequence complementary to one or more additional target nucleic acids. In some cases, the capturing further comprises enriching the target nucleic acid, wherein the enriching comprises performing PCR by adding a set of primers and PCR reagents to the proximity junctions hybridized with the oligonucleotide comprising sequence complementary to the target nucleic acid, wherein each primer in the set of primers comprises random sequence. In some cases, the oligonucleotide and each primer in the set of primers further comprise adaptor sequences compatible with a next generation sequencing (NGS) system. In some cases, the analyzing comprises sequencing the one or more nucleic acids in the proximity junctions. In some cases, the analyzing comprises labeling the one or more nucleic acids present in the proximity junctions. In some cases, the labeled one or more nucleic acids are hybridized to a microarray. In some cases, the target nucleic acid is an antibiotic resistance gene. In some cases, the sample comprising the mixed cell population is derived from the site of an infection in an individual. In some cases, the sample comprising the mixed cell population is derived from an agricultural sample. In some cases, the agricultural sample is cow rumen or manure. In some cases, the target nucleic acid is present in a plasmid, virus or genomic DNA. In some cases, each of the one or more nucleic acids is present in a plasmid, virus or genomic DNA. In some cases, the target nucleic acid is an oncogene or a tumor suppressor gene. In some cases, the sample comprising the mixed population is a tumor sample.

In another aspect, provided herein is a method for detecting one or more nucleic acids associated with an antibiotic resistance gene comprising: generating proximity junctions between one or more nucleic acids and an antibiotic resistance gene in a cell, wherein the cell is present in a sample comprising a mixed cell population; capturing the proximity junctions between the one or more nucleic acids and the antibiotic resistance gene, wherein the capturing comprises hybridizing the proximity junctions with an oligonucleotide comprising sequence complementary to the antibiotic resistance gene; and analyzing the one or more nucleic acids in the proximity junctions hybridized to the oligonucleotide comprising sequence complementary to the antibiotic resistance gene, thereby determining the presence of the one or more nucleic acids in the cell comprising the antibiotic resistance gene. In some cases, the generation of the proximity junctions between one or more nucleic acids and the antibiotic resistance gene comprises: i.) incubating the sample comprising the cell with a cross-linking agent, wherein the cross-linking agent cross-links proteins and the one or more nucleic acids with the antibiotic resistance gene in the cell, thereby generating a complex between the one or more nucleic acids and the antibiotic resistance gene; ii.) lysing the cell in a lysing buffer comprising a combination of one or more anionic detergents and one or more non-ionic detergents; iii.) digesting the nucleic acid within the complex between the one or more nucleic acids and the oncogene, thereby generating free nucleic acid ends; iv.) ligating the digested nucleic acid; and v.) releasing the one or more proximity junctions from the cross-linked protein, thereby generating the proximity junctions between the one or more nucleic acids and the antibiotic resistance gene. In some cases, the cross-linking reagent comprises formaldehyde. In some cases, the method further comprises the step of incubating the complex with a cross-linking quencher. In some cases, the cross-linking quencher is glycine. In some cases, the endonuclease is a restriction endonuclease. In some cases, the endonuclease is DNase. In some cases, the endonuclease is MNase. In some cases, the releasing comprises reversing cross-linking by treating the cross-linked proteins with an agent selected from protease, heat or a combination thereof. In some cases, the releasing comprises fragmenting the complex. In some cases, the oligonucleotide comprising sequence complementary to the antibiotic resistance gene further comprises a moiety attached to a 5' end. In some cases, the moiety is biotin. In some cases, the oligonucleotide comprising sequence complementary to the antibiotic resistance gene is bound to a solid substrate. In some cases, the solid substrate is selected from a bead, a well in a multi-well plate or surface of a slide. In some cases, the bead is a magnetic bead. In some cases, the method further comprises labeling the free nucleic ends with biotin prior to step v.), whereby the proximity junctions generated following step v.) are biotin labeled. In some cases, the proximity junctions that are biotin labeled are subjected to a purification step prior to capturing the proximity junctions, wherein the purification step comprises binding biotin with avidin or streptavidin attached to a solid substrate. In some cases, the capturing further comprises enriching the antibiotic resistance gene wherein the enriching comprises performing polymerase chain reaction (PCR) by adding a set of primers and PCR reagents to the proximity junctions hybridized with the oligonucleotide comprising sequence complementary to the antibiotic resistance gene, wherein each primer in the set of primers comprises sequence complementary to one or more additional target nucleic acids. In some cases, the capturing further comprises enriching the antibiotic resistance gene, wherein the enriching comprises performing PCR by adding a set of primers and PCR reagents to the proximity junctions hybridized with the oligonucleotide comprising sequence complementary to the antibiotic resistance gene, wherein each primer in the set of primers comprises random sequence. In some cases, the oligonucleotide and each primer in the set of primers further comprise adaptor sequences compatible with a next generation sequencing (NGS) system. In some cases, the analyzing comprises sequencing the one or more nucleic acids in the proximity junctions. In some cases, the analyzing comprises labeling the one or more nucleic acids present in the proximity junctions. In some cases, the labeled one or more nucleic acids are hybridized to a microarray. In some cases, the antibiotic resistance gene is present in a plasmid or the genome of the cell. In some cases, each of the one or more nucleic acids is present in a plasmid or the genome of the cell. In some cases, the sample is derived from the site of an infection in an individual. In some cases, the sample is derived from an agricultural sample. In some cases, the agricultural sample is cow rumen or manure.

In yet another aspect, provided herein is a method for detecting one or more nucleic acids associated with an oncogene or a tumor suppressor gene comprising: generating proximity junctions between one or more nucleic acids and an oncogene or tumor suppressor gene in a cell, wherein the cell is present in a sample comprising a mixed cell population derived from an individual; capturing the proximity junctions between the one or more nucleic acids and the oncogene or the tumor suppressor gene, wherein the capturing comprises hybridizing the proximity junctions with an oligonucleotide comprising sequence complementary to the oncogene or the tumor suppressor gene; and analyzing the one or more nucleic acids in the proximity junctions hybridized to the oligonucleotide comprising sequence complementary to the oncogene or the tumor suppressor gene, thereby determining the presence of the one or more nucleic acids in the cell comprising the oncogene or the tumor suppressor gene. In some cases, the generation of the proximity junctions between one or more nucleic acids and the oncogene or the tumor suppressor gene comprises: i.) incubating the sample with a cross-linking agent, wherein the cross-linking agent cross-links proteins and the one or more nucleic acids and the oncogene or the tumor suppressor gene in the cell, thereby generating a complex between the one or more nucleic acids and the oncogene or the tumor suppressor gene; ii.) lysing the cell in a lysing buffer comprising a combination of one or more anionic detergents and one or more non-ionic detergents; iii.) digesting the nucleic acid within the complex between the one or more nucleic acids and the oncogene or the tumor suppressor gene, thereby generating free nucleic acid ends; iv.) ligating the digested nucleic acid; and v.) releasing the one or more proximity junctions from the cross-linked protein, thereby generating the proximity junctions between the one or more nucleic acids and the oncogene or the tumor suppressor gene. In some cases, the cross-linking reagent comprises formaldehyde. In some cases, the method further comprises the step of incubating the complex with a cross-linking quencher. In some cases, the cross-linking quencher is glycine. In some cases, the endonuclease is a restriction endonuclease. In some cases, the endonuclease is DNase. In some cases, the endonuclease is MNase. In some cases, the releasing comprises reversing cross-linking by treating the cross-linked proteins with an agent selected from protease or heat. In some cases, the releasing comprises fragmenting the complex. In some cases, the oligonucleotide comprising sequence complementary to the oncogene or the tumor suppressor gene further comprises a moiety attached to a 5' end. In some cases, the moiety is biotin. In some cases, the oligonucleotide comprising sequence complementary to the oncogene or the tumor suppressor gene is bound to a solid substrate. In some cases, the solid substrate is selected from a bead, a well in a multi-well plate or surface of a slide. In some cases, the bead is a magnetic bead. In some cases, the method further comprises labeling the free nucleic ends with biotin prior to step v.), whereby the proximity junctions generated following step v.) are biotin labeled. In some cases, the proximity junctions that are biotin labeled are subjected to a purification step prior to capturing the proximity junctions, wherein the purification step comprises binding biotin with avidin or streptavidin attached to a solid substrate. In some cases, the capturing further comprises enriching the oncogene wherein the enriching comprises performing polymerase chain reaction (PCR) by adding a set of primers and PCR reagents to the proximity junctions hybridized with the oligonucleotide comprising sequence complementary to the oncogene, wherein each primer in the set of primers comprises sequence complementary to one or more additional target nucleic acids. In some cases, the capturing further comprises enriching the oncogene or the tumor suppressor gene, wherein the enriching comprises performing PCR by adding a set of primers and PCR reagents to the proximity junctions hybridized with the oligonucleotide comprising sequence complementary to the oncogene or the tumor suppressor gene, wherein each primer in the set of primers comprises random sequence. In some cases, the oligonucleotide and each primer in the set of primers further comprise adaptor sequences compatible with a next generation sequencing (NGS) system. In some cases, the analyzing comprises sequencing the one or more nucleic acids in the proximity junctions. In some cases, the analyzing comprises labeling the one or more nucleic acids present in the proximity junctions. In some cases, the labeled one or more nucleic acids are hybridized to a microarray. In some cases, the sample comprising the mixed population is a tumor sample.

BRIEF DESCRIPTION OF THE DRAWINGS

FIG. 1 shows selecting and detecting using capture primers (or oligonucleotides) comprising beads attached thereto (e.g., biotin) that are annealed to a sequence of interest, isolating the capture primers (for example, using magnetic beads) and extending sequences covering proximity junctions using PCR or an elongating/displacing polymerase. The recovered DNA molecules are analyzed using microarray or sequencing (e.g., next-generation sequencing). Alternatively, the capture oligonucleotides or primers can be preloaded to the beads (e.g., magnetic beads) prior to annealing and the proximity ligated junctions are loaded to the beads to form bead bound complexes that are heated and annealed in place, then elongated. The elongation can be done in the presence of a label (e.g., Cy3), thereby leaving the beads with labelled (e.g., green) probes.

FIG. 2A-2D illustrates the use of a capture Hi-C method as provided herein to enrich target sequences and Hi-C interactions. FIG. 2A shows the sequencing coverage distribution of 100 randomly selected regions within the *E. coli* and *B. subtilis* genomes. The vertical line indicates the coverage observed for captured sequences indicating a >1 standard deviation of the mean coverage. FIG. 2B shows the fraction of read pairs mapping to two different regions of the *E. coli* and *B. subtilis* genomes following capture with their respective probes.

FIG. 2C shows the fraction of read pairs mapping greater than 10 kb from each other, another indicator of the fraction of reads showing Hi-C signal. FIG. 2D shows the fraction of read pairs mapping 0 base pairs from each other in the reference genome sequence, indicating non-Hi-C reads.

DETAILED DESCRIPTION OF THE INVENTION

Definitions

Figure 1:
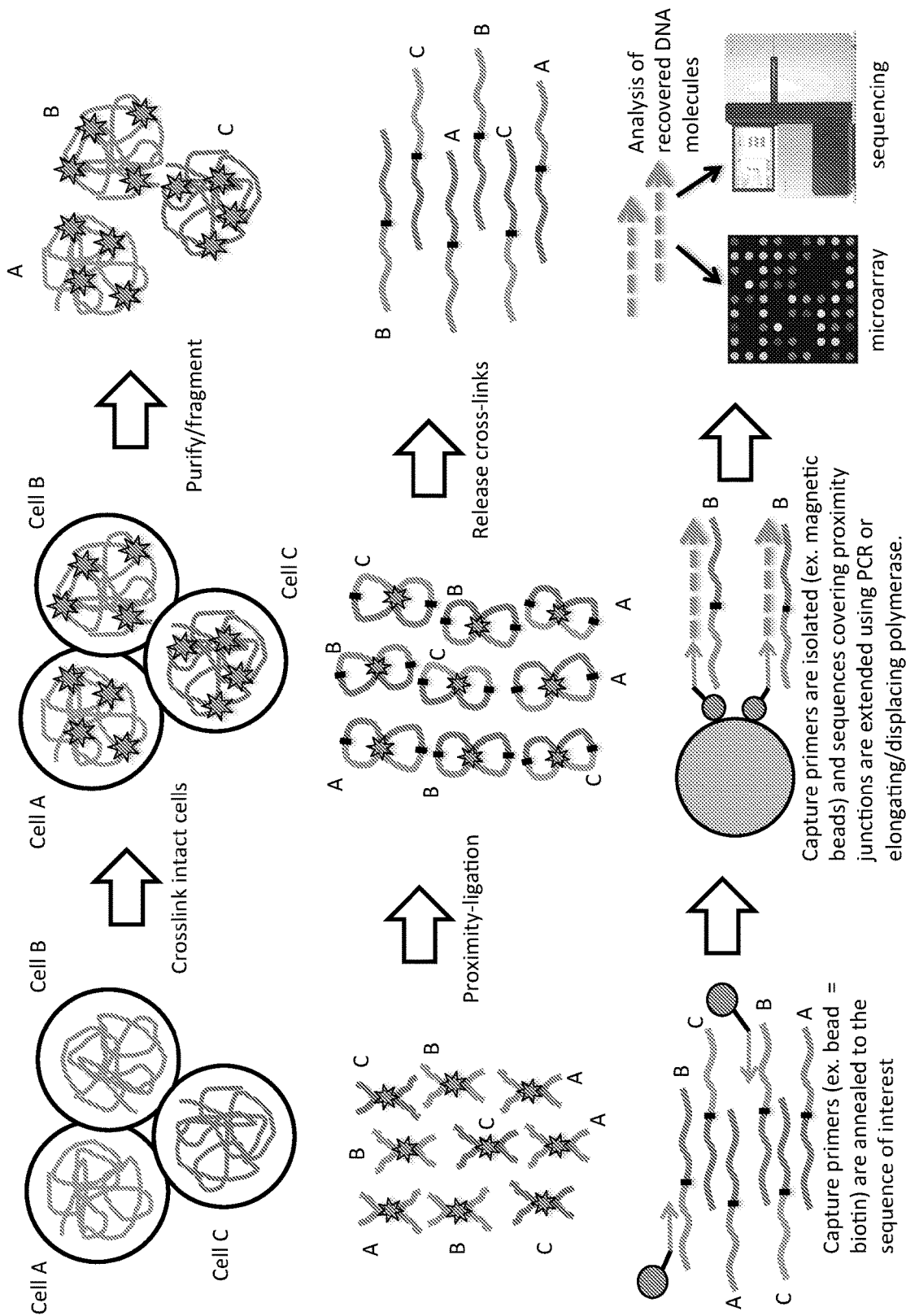
FIG. 1 illustrates a method for determining or detecting the presence of nucleic acids (e.g., DNA) in a cell associated with and/or adjacent to a target sequence of interest using proximity-ligation in combination with nucleic acid (e.g., DNA) capture technology. In general, a mixed population of cells (e.g., Cells A, B and C) is treated with a crosslinker, trapping nearby DNA molecules inside cells, crosslinked chromatin is purified from the cell population and subsequently fragmented, proximity-ligation is performed to create chimeric DNA junctions between sequences that were in the same cell, the crosslinks are reversed, thereby (e.g., reversed) freeing the proximity ligated junctions, and specific proximity junctions are selected and detected.

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Unless the context requires otherwise, throughout the present specification and claims, the word "comprise" and variations thereof, such as, "comprises" and "comprising" are to be construed in an open, inclusive sense that is as "including, but not limited to". The use of the alternative (e.g., "or") should be understood to mean either one, both, or any combination thereof of the alternatives. As used herein, the terms "about" and "consisting essentially of" mean +/−20% of the indicated range, value, or structure, unless otherwise indicated.

Reference throughout this specification to "one embodiment" or "an embodiment" means that a particular feature, structure or characteristic described in connection with the embodiment may be included in at least one embodiment of the present disclosure. Thus, the appearances of the phrases "in one embodiment" or "in an embodiment" in various places throughout this specification may not necessarily all be referring to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

Throughout this disclosure, various aspects of the methods and compositions provided herein can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Unless otherwise indicated, the methods and compositions provided herein can utilize conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Gait, "Oligonucleotide Synthesis: A Practical Approach" 1984, IRL Press, London, Nelson and Cox (2000), Lehninger et al., (2008) Principles of Biochemistry 5th Ed., W.H. Freeman Pub., New York, N.Y. and Berg et al. (2006) Biochemistry, $6^{th}$ Ed., W.H. Freeman Pub., New York, N.Y., all of which are herein incorporated in their entirety by reference for all purposes.

Conventional software and systems may also be used in the methods and compositions provided herein. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes, etc. The computer-executable instructions may be written in a suitable computer language or combination of several languages. Basic computational biology methods are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001). See U.S. Pat. No. 6,420,108.

The methods and compositions provided herein may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Computer methods related to genotyping using high density microarray analysis may also be used in the present methods, see, for example, US Patent Pub. Nos. 20050250151, 20050244883, 20050108197, 20050079536 and 20050042654.

Additionally, the present disclosure may have preferred embodiments that include methods for providing genetic information over networks such as the Internet as shown in U.S. Patent Pub. Nos. 20030097222, 20020183936, 20030100995, 20030120432, 20040002818, 20040126840, and 20040049354.

An allele can refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles can be referred to as "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

The term "array" as used herein can refer to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, microparticles, nanoparticles or other solid supports.

The term "complementary" as used herein can refer to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. See, M. Kanehisa Nucleic Acids Res. 12:203 (1984), incorporated herein by reference.

The term "hybridization" as used herein can refer to the process in which two single-stranded polynucleotides bind noncovalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization."

Hybridizations may be performed under stringent conditions, for example, at a salt concentration of no more than 1 M and a temperature of at least 25. degree. C. For example, conditions of 5. times. SSPE (750 mM NaCl, 50 mM NaPhosphate, 5 mM EDTA, pH 7.4) and a temperature of 25-30. degree. C. are suitable for allele-specific probe hybridizations. For stringent conditions, see, for example, Sambrook, Fritsche and Maniatis. "Molecular Cloning A laboratory Manual" 2.sup.nd Ed. Cold Spring Harbor Press (1989) which is hereby incorporated by reference in its entirety for all purposes above. In some aspects salt concentrations for hybridization are preferably between about 200 mM and about 1M or between about 200 mM and about 500 mM. Hybridization temperatures can be as low as 5. degree. C., but are typically greater than 22. degree. C., more typically greater than about 30. degree. C., and preferably in excess of about 37. degree. C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Methods for conducting polynucleotide hybridization assays in the methods and compositions provided herein can be any known and developed in the art. Hybridization assay procedures and conditions can vary depending on the application and can be selected in accordance with known general binding methods, including those referred to in: Maniatis et al. Molecular Cloning: A Laboratory Manual (2.sup.nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The method and compositions provided herein can also utilize signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625 in U.S. Patent Pub. No. 20040012676 and in PCT Application PCT/US99/06097 (published as WO99/47964), each of which also is hereby incorporated by reference in its entirety for all purposes.

Methods and apparatus for signal detection and processing of intensity data can be those disclosed in, for example, U.S. Pat. Nos. 5,143,854, 5,547,839, 5,578,832, 5,631,734, 5,800,992, 5,834,758, 5,856,092, 5,902,723, 5,936,324, 5,981,956, 6,025,601, 6,090,555, 6,141,096, 6,185,030, 6,201,639; 6,218,803; and 6,225,625, in U.S. Patent Pub. Nos. 20040012676 and 20050059062 and in PCT Application PCT/US99/06097 (published as WO99/47964), each of which also is hereby incorporated by reference in its entirety for all purposes.

The term "mixed population" or sometimes refer by "complex population" as used herein can refer to any sample containing both desired and undesired nucleic acids or cells. As a non-limiting example, a complex population of nucleic acids may be total genomic DNA, total genomic RNA or a combination thereof. The total genomic DNA or RNA may be derived from one, a plurality or all of the cells within a mixed population of cells. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "mRNA" or "mRNA transcripts" as used herein, can include, but is not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid" as used herein can refer to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs can be those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs can be derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "oligonucleotide" or "polynucleotide" as used herein can refer to a nucleic acid ranging from at least 2, preferable at least 8, and more preferably at least 20 nucleotides in length or a compound that specifically hybridizes to a polynucleotide. Polynucleotides of the methods and compositions provided herein can include sequences of deoxyribonucleic acid (DNA) or ribonucleic acid (RNA) which may be isolated from natural sources, recombinantly produced or artificially synthesized and mimetics thereof. A further example of a polynucleotide of the methods and compositions provided herein invention may be peptide nucleic acid (PNA). The methods and compositions provided herein can also encompass situations in which there is a nontraditional base pairing such as Hoogsteen base pairing which has been identified in certain tRNA molecules and postulated to exist in a triple helix. "Polynucleotide" and "oligonucleotide" can be used interchangeably in the methods and compositions provided herein.

The term "polymorphism" as used herein can refer to the occurrence of two or more genetically determined alternative sequences or alleles in a population. A polymorphic marker or site can be the locus at which divergence occurs. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form can be arbitrarily designated as the reference form and other allelic forms can be designated as alternative or variant alleles. The allelic form occurring most frequently in a selected population can sometimes be referred to as the wildtype form. Diploid organisms may be homozygous or heterozygous for allelic forms. A diallelic polymorphism can have two forms. A triallelic polymorphism can have three forms. Single nucleotide polymorphisms (SNPs) can be included in polymorphisms.

The term "primer" as used herein can refer to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules can generally require cooler temperatures to form sufficiently stable hybrid complexes with the template. A primer need not reflect the exact sequence of the template but must be sufficiently complementary to hybridize with such template. The primer site can be the area of the template to which a primer hybridizes. The primer pair can be a set of primers including a 5' upstream primer that hybridizes with the 5' end of the sequence to be amplified and a 3' downstream primer that hybridizes with the complement of the 3' end of the sequence to be amplified.

The term "solid support", "solid substrate", "support", and "substrate" as used herein can be used interchangeably and can refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 and US Patent Pub. Nos. 20090149340 and 20080038559 for exemplary substrates.

Overview

Provided herein are methods and compositions for determining or detecting the presence of one or more nucleic acids in association with a target nucleic acid. The one or more nucleic acids and/or target nucleic acid can be derived or originate from the same cell within a mixed population of cells. The methods provided herein can permit the identification of nucleic acid (e.g., DNA) sequences in association with a target nucleic acid in a manner that is more efficient and less time consuming than methods currently known in the art. In some cases, the method can allow rapid, sequencing-free querying of whether certain sequences or alleles of nucleic acid (e.g., DNA) co-exist within the same cell in a mixed population even if those sequences are located on different chromosomes or plasmids.

The methods provided herein can be used to deconvolute any mixed population of cells or nucleic acids. For example, the methods provided herein can be used for deconvoluting mixed populations of microbial cells or communities. Additionally, the methods provided herein may be used to ask which alleles are present in the same cells within a solid tumor. Other, non-limiting examples of mixed populations of cells or nucleic acids for use by the methods and compositions provided herein may be whole organs/blood, contaminated or mixed forensic samples.

In one embodiment, the methods and compositions provided herein may serve as a basis for a diagnostic test such that a query gene of interest can be tethered to capture beads and a microarray can be designed for a set of nucleic acids from a known source (e.g., cell or pool of nucleic acids). The diagnostic test can be for detecting antibiotic microbial resistance genes such that the known source can be a known strain or species of microbe. The cross-linked chromatin generated during the method can create proximity junctions between pairs of nucleic acid (e.g., DNA) sequences within the same cell. These junctions can be selected with capture or PCR reagents and then hybridized to a microarray probe (or sequenced) to tell whether the captured sequence interacted intra-cellularly with any or multiple nucleic acids on the microarray (or sequence database).

In contrast to methods known in the art (e.g., Hi-C), the method provided herein does not assemble de novo genomes, but can drastically reduce the cost of the process (by eliminating sequencing, or when sequencing is preserved, by drastically reducing the complexity of the sequence library). Additionally, the method provided herein can be significantly faster and cheaper than Hi-C and can be much more scalable for diagnostic purposes.

As shown in FIG. 1, the methods provided herein generally comprise:

1. Subjecting nucleic acids and/or proteins within cells in a mixed cell population (e.g., cells A, B and C in FIG. 1) to crosslinking agents (e.g., formaldehyde). The cross-linked nucleic acid and/or protein complexes (e.g., chromatin) can then be released or purified from the cell population. See, for example, FIG. 1 where the cross-linked chromatin from each cell is released from the cell (labelled as "A", "B" and "C" in FIG. 1 to denote chromatin derived from cell A, B or C, respectively). The purified cross-linked complexes (e.g., chromatin) can then be fragmented.

2. Joining or ligating DNA ends generated from cross-linked molecules to create proximity-junctions. In some cases, the DNA ends may be biotinylated prior to ligation in order to create junctions that can be purified with affinity beads in a subsequent step. Importantly, junctions will not form between sequences that originated in different strains/species/cells.

3. Releasing the proximity junctions from cross-linked chromatin.

4. Selecting the proximity junctions and detecting one or more nucleic acid sequences adjacent to or in proximity to a target sequence of interest.

Cross-Linking

In one embodiment, the crosslinks are selected from the group including, but not limited to, nucleic acid-nucleic acid crosslinks or protein-nucleic acid crosslinks. Examples of cross-linking agents suitable for the methods provided herein can include, but are not limited to alkylating agents, such as 1, 3-bis(2-chloroethyl)-1-nitrosourea (BCNU, carmustine)) and nitrogen mustard, cisplatin (cis-diamminedichloroplatinum(II)) and its derivatives, psoralens, acrolein, crotonaldehyde, formaldehyde, glutaraldehyde, or a combination thereof. In some cases, the cross-linking agent is formaldehyde, glutaraldehyde or a combination thereof.

In one embodiment, the cell treated with the cross-linking agent comprises a non-mammalian cell. In one embodiment, the non-mammalian cell comprises a cell selected from the group including, but not limited to, fish, amphibian, insects, birds, yeast, fungi, bacteria, or mold. In one embodiment, the cell comprises a mammalian cell. In one embodiment, the mammalian cell comprises a human cell. In one embodiment, the mammalian cell is a tumor or cancer cell. In one embodiment, the tumor or cancer cell is part of a mixed population of tumor cells. In one embodiment, the cell comprises a microbial cell. In one embodiment, the microbial cell is part of a mixed microbial population. The cells treated with or subjected to the cross-linking agent or cross-linker can be, for example, a mixed microbial population or tumor sample. The cells can be intact.

Intact cells can be permeabilized following treatment with the cross-linking agents in order to allow additional agents (e.g., detection agents) to enter the cell(s). Permeabilization can be performed by treating the cell(s) with a permeabilization agent. Examples of permeabilization agents for use in the methods provided herein can be any permeabilization agent known in the art, such as, for example, organic solvents or detergents. The organic solvents can be methanol or acetone. The detergent can be saponin, Triton X-100 or Tween-20.

In one embodiment, cross-linking can create cross-linked junctions between nearby pairs of nucleic acid sequences or molecules (e.g., DNA) within cells (importantly, never between cells). Some junctions can be between nucleic acid or gene sequences on the same nucleic acid molecule. In some cases, the junctions can be between genes on one or more plasmids and host cell genes present within genomic DNA. In some cases, the junctions can be between nucleic acid sequences or genes on multiple chromosomes.

Digestion of Cross-Linked Junctions

In some cases, cross-linked junctions (e.g., cross-linked chromatin) generated using the methods provided herein can be digested to create DNA ends. The DNA ends can be joined or ligated to each other in a subsequent step. Digestion of the cross-linked junctions can be performed using an enzyme such as, for example, a restriction enzyme or an endonuclease (e.g., DNAse I or MNase). In some cases, fragmentation of the cross-linked junctions generates overhanging or 'sticky' DNA ends. The overhanging or 'sticky' ends can be 'filled in' or made blunt. The filing in can be accomplished using any methods or enzymes known in the art, such as, for example, the Klenow fragment. In some cases, fragmentation is accomplished by restriction enzyme digestion and overhanging ends are filled in using the Klenow fragment of E. coli DNA polymerase I.

Joining/Ligating of DNA Ends

Following digestion and generation of DNA ends, the generated DNA ends can be covalently attached to produce a single larger polynucleotide with a contiguous backbone. Methods for joining the DNA ends are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, the DNA ends are joined by ligation via a ligase, such as, for example, a DNA ligase or RNA ligase. Multiple ligases, each having characterized reaction conditions, are known in the art, and include, without limitation NAD-dependent ligases including tRNA ligase, Taq DNA ligase, Therrnusfi4fonnis DNA ligase. *Escherichia coli* DNA ligase, Tth DNA ligase, *Thermus scoroducws* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pth DNA ligase, DNA ligase 1, DNA ligase Ill, DNA ligase IV, and novel ligases discovered by bioprospecting; and wild-type, mutant isofornis, and genetically engineered variants thereof. Digestion of the cross-linked junctions can generate DNA ends with hybridizable sequences, such as complementary overhangs and thereby be useful for sticky-end ligation. Digestion of the cross-linked junctions can generate DNA ends that are blunt, and thereby be useful for blunt-end ligation. Generally, a 5' phosphate is utilized in a ligation reaction. The 5' phosphate can be provided by one of the generated DNA ends or both. 5' phosphates can be added to or removed from the DNA ends to be joined, as needed.

Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, both of the two ends joined in a ligation reaction provide a 5' phosphate, such that two covalent linkages are made in joining the two ends. In some embodiments, only one of the two ends joined in a ligation reaction provides a 5' phosphate, such that only one covalent linkage is made in joining the two ends. In some embodiments, 3' phosphates are removed prior to ligation.

As previously described, the DNA ends may be biotinylated prior to ligation in order to create junctions that are biotin labeled.

Releasing the Junctions

As discussed herein, following the generation of proximity junctions, the cross-linked nucleic acids can be subjected to a releasing of the cross-links. The releasing of the cross-links can facilitate capture of the target sequence of interest (i.e., "query gene") and subsequent detection of any and all nucleic acids associated therewith or located in proximity to the target sequence of interest. The releasing can be done either by reversing crosslinks to release all DNA or by fragmenting the cross-linked/ligated chromatin to release the naked DNA proximity junctions. Reversal of the cross-links can be achieved using any method known in the art. For example, the cross-links can be reversed using enzymatic or non-enzymatic means. Non-limiting examples of enzymatic means for cross-link reversal include treatment with restriction enzymes, proteases or proteinase K, while a non-limiting example of a non-enzymatic cross-link reversal means includes heat treatment. In some cases, the reversing the cross-linking comprises heating the cross-links to at least about 55° C., at least about 65° C., or at least about 95° C. In some cases, reversing the cross-linking comprises incubating the partitions with a proteinase, such as proteinase K. In some cases, a combination of enzymatic (e.g., protease or proteinase K) and non-enzymatic means (e.g., heat treatment) are used to reverse the cross-links. Alternatively, the cross-links can be subjected to sonication to fragment the cross-linked/joined (e.g., ligated) chromatin and thereby release the naked proximity junctions. In some cases, the cross-linker used to generate said cross-links is reversible, such as, for example, psoralen, such that reversal of the cross-linking can be accomplished by changing the pH or photo-reversing the cross-links using, for example, UV light.

In some embodiments, the proximity junctions can be enriched prior to purification and detection. In one embodiment, biotin labels are appended to the proximity junctions as described herein and hybridized to or bound to substrates coated or coupled to avidin or streptavidin moieties such as, for example, affinity beads. Subsequently, non-bound complexes are washed or separated away from the biotin/avidin (streptavidin) complexes. The biotin selection can serve to remove significant amounts of background DNA prior to the selection or purification of the proximity junctions.

Selection and Detection

Following releasing and/or enriching of the proximity junctions, the one or more sequences associated, co-localized or in proximity to a query sequence of interest can be selected or purified and subsequently detected. In some embodiments, the proximity junctions are enriched with DNA capture technology (similar to exome purification). In one embodiment, a query sequence of interest is selected or purified by being exposed to a capture oligonucleotide (see, for example, the capture primers in FIG. 1) that comprises sequence complementary to the query sequence of interest. In one embodiment, the complementary sequences in the oligonucleotides used to capture the relevant proximity junctions can be changed for different query genes or sequences of interest and/or can be a pool of capture oligonucleotides, each comprising a distinct or different sequence around a gene of interest.

In one embodiment, a capture oligonucleotide comprising sequence complementary to a query or target sequence of interest has a moiety attached thereto. The moiety is preferably attached at the 5' end of the capture oligonucleotide. In one embodiment, the moiety is biotin (see, for example, FIG. 1). In one embodiment, a capture oligonucleotide comprising sequence complementary to the query sequence of interest further comprises a moiety (e.g., biotin) attached to its 5' end. Further to this embodiment, the capture oligonucleotide is introduced to the released proximity junctions under conditions conducive or permissive for hybridization. The capture oligonucleotide can bind to those proximity junctions (e.g., DNA junctions) where at least one side or part of the junction comprises the query sequence complementary to the sequence present in the capture oligonucleotide, thereby generating complexes comprising the capture oligonucleotide bound to at least one side or part of the proximity junction. The complexes can then be isolated or purified by complexing the moiety on the capture oligonucleotide (e.g., on the 5' end) with a solid substrate or matrix. In cases where the capture oligonucleotides are labelled with biotin, the complexing can be facilitated through the use of a solid matrix or matrix coated or complexed with avidin or streptavidin. The substrate or matrix can be a bead such as, for example, magnetic beads or affinity beads.

In another embodiment, a capture oligonucleotide comprising sequence complementary to the query sequence of interest is attached to a solid substrate or matrix (e.g., affinity beads or magnetic beads) prior to being introduced to the released proximity junctions. In this case, it can be said that the solid substrate or matrix is pre-loaded with the capture oligonucleotide. In cases where the capture oligonucleotides are labelled with biotin, pre-loading can be facilitated through the use of a solid substrate or matrix coated or complexed with avidin or streptavidin. The released proximity junctions can then be exposed to said solid substrate or matrix comprising the sequence complementary to the query sequence of interest under conditions conducive or permissive for hybridization. The substrate or matrix can bind to those proximity junctions (e.g., DNA junctions) where at least one side or part of the junction comprises the query sequence complementary to the sequence that is attached to the solid substrate or matrix (e.g., "query gene", such as an antibiotic-resistance gene).

Further to the above embodiments, purifying the matrix/beads can thus serve to purify the junctions comprising the query sequence. Following capture of the desired proximity junction(s), the one or more sequences present in the proximity junctions with the query sequence of interest can be labelled. As shown in FIG. 1, the sequences covering proximity junctions can be extended using PCR or elongating/displacing polymerases. The labeling can serve to allow detection of said one or more sequences by either sequencing (e.g., NGS) or by hybridization to microarrays comprising sequences complementary to the labeled one or more sequences (in order to assay the presence of sequences of interest on the "other side" of the junction). Labeling of the one or more sequences can be performed using any method known in the art such as, for example, using PCR with one or more labeled nucleotides (e.g., Cy3 or Cy5 labeled dUTP). Detection of the binding of the labeled one or more sequences to sequence(s) on the microarray can be detected using any method known in the art.

In another embodiment, the proximity junctions comprising a query sequence can be selected or purified by PCR such that the complement of a query sequence of interest is placed on one primer, while a second primer or set of second primers can be directed toward a random sequence or a mixed pool of known sequences. In this embodiment, the second primer or set of second primers can be varied to be random or can be limited to a mixed pool of primers directed to known sequences. In some cases, the one or more sequences present in the proximity junctions with the query sequence of interest can be labelled. The labeling can serve to allow detection of said one or more sequences upon binding of said labeled one or more sequences to a microarray comprising sequences complementary to the labeled one or more sequences. Labeling of the one or more sequences can be performed using any method known in the art such as, for example, using PCR with one or more labeled nucleotides (e.g., Cy3 or Cy5 labeled dUTP). Detection of the binding of the labeled one or more sequences to sequence(s) on the microarray can be detected using any method known in the art.

In yet another embodiment, selection entails the use of PCR as described herein such that the first and/or second primer(s) can have sequencing adapter sequence appended thereto. The presence of the sequencing adapter sequence can enable rapid creation of a sequencing library. The sequencing library can subsequently be loaded into a sequencer and sequenced. The sequencer can be compatible with any type of sequencing known in the art. In some cases, the type of sequencing is a known next generation sequencing (NGS) method and system for use thereof. For example, the NGS sequencing can be Illumina® sequencing, polony sequencing, 454 pyrosequencing, SOLiD sequencing, Ion Torrent semiconductor sequencing, DNA nanoball sequencing, Heliscope single molecule sequencing, single molecule real time (SMRT) sequencing or Nanopore DNA sequencing.

Detection of Microbial Antibiotic Resistance Genes

In one embodiment, the methods provided herein are utilized to detect or determine the association or presence of one or more microbial genes with a target nucleic acid (i.e., query sequence of interest) in a sample comprising one or a mixed population of microbial cells. The one or more microbial genes can be co-localized, adjacent to or in proximity to the target nucleic acid within a cell (e.g., microbial cell) in the sample. The sample can be any sample that contains microbial cells or a mixed population thereof such as, for example, a site of infection within an individual or patient. The one or more microbial genes and/or target nucleic acid can be genomic DNA or a gene located on a plasmid or other extrachromosomal entity. The one or more microbial genes and/or target nucleic acid can be a toxic microbial gene. In one embodiment, the one or more microbial genes and/or target nucleic acid are antibiotic resistance genes. The antibiotic resistance genes can be any gene conferring resistance to an antibiotic known in the art. The antibiotic can be selected from aminoglycosides, beta-lactams, macrolide-lincosamide-streptogramin B (MLSB), tetracycline, vancomycin. The antibiotic resistance genes can be any antibiotic resistance gene known in the art. For example, the antibiotic resistance gene can be any multidrug transporter gene. The antibiotic resistance gene can be, for example, selected from aac2ia, aac2ib, aac2ic, aac2id, aac2i, aac3ia, aac3iia, aac3iib, aac3iii, aac3iv, aac3ix, aac3vi, aac3viii, aac3vii, aac3x, aac6i, aac6ia, aac6ib, aac6ic, aac6ie, aac6if, aac6ig, aac6iia, aac6iib, aad9, aad9ib, aadd, acra, acrb, adea, adeb, adec, amra, amrb, ant2ia, ant2ib, ant3ia, ant4iia, ant6ia, aph33ia, aph33ib, aph3ia, aph3ib, aph3ic, aph3iiia, aph3iva, aph3va, aph3vb, aph3via, aph3viia, aph4ib, aph6ia, aph6ib, aph6ic, aph6id, arna, baca, bcra, bcrc, bl1_acc, bl1_ampc, bl1_asba, bl1_ceps, bl1_cmy2, bl1_ec, bl1_fox, bl1_mox, bl1_och, bl1_pao, bl1_pse, bl1_sm, bl2a_1, bl2a_exo, bl2a_iii2, bl2a_iii, bl2a_kcc, bl2a_nps, bl2a_okp, bl2_apc, bl2be_ctxm, bl2be_oxyl, bl2be_per, bl2be_shv2, bl2b_rob, bl2b_tem1, bl2b_tem2, bl2b_tem, bl2b_tle, bl2b_ula, bl2c_bro, bl2c_pse1, bl2c_pse3, bl2d_lcrl, bl2d_moxa, bl2d_oxa10, bl2d_oxa1, bl2d_oxa2, bl2d_oxa5, bl2d_oxa9, bl2d_r39, bl2e_cbla, bl2e_cepa, bl2e_cfxa, bl2e_fpm, bl2e_y56, bl2f_nmca, bl2f_smel, bl2_ges, bl2_kpc, bl2_len, bl2_veb, bl3_ccra, bl3_cit, bl3_cpha, bl3_gim, bl3_imp, bl3_l, bl3_shw, bl3_sim, bl3_vim, ble, blt, bmr, cara, cata10, cata11, cata12, cata13, cata14, cata15, cata16, cata1, cata2, cata3, cata4, cata5, cata6, cata7, cata8, cata9, catb1, catb2, catb3, catb4, catb5, ceoa, ceob, cml_e1, cml_e2, cml_e3, cml_e4, cml_e5, cml_e6, cml_e7, cml_e8, dfra10, dfra12, dfra13, dfra14, dfra15, dfra16, dfra17, dfra19, dfra1, dfra20, dfra21, dfra22, dfra23, dfra24, dfra25, dfra25, dfra25, dfra26, dfra5, dfra7, dfrb1, dfrb2, dfrb3, dfrb6, emea, emrd, emre, erea, ereb, erma, ermb, ermc, ermd, erme, ermf, ermg, ermh, ermn, ermo, ermq, ermr, erms, ermt, ermu, ermv, ermw, ermx, ermy, fosa, fosb, fosc, fosx, fusb, fush, ksga, lmra, lmrb, lnua, lnub, lsa, maca, macb, mdte, mdtf, mdtg, mdth, mdtk, mdtl, mdtm, mdtn, mdto, mdtp, meca, mecrl, mefa, mepa, mexa, mexb, mexc, mexd, mexe, mexf, mexh, mexi, mexw, mexx, mexy, mfpa, mpha, mphb, mphc, msra, norm, oleb, opcm, opra, oprd, oprj, oprm, oprn, otra, otrb, pbp1a, pbp1b, pbp2b, pbp2, pbp2x, pmra, qac, qaca, qacb, qnra, qnrb, qnrs, rosa, rosb, smea, smeb, smec, smed, smee, smef, srmb, sta, str, sul1, sul2, su13, tcma, tcr3, tet30, tet31, tet32, tet33, tet34, tet36, tet37, tet38, tet39, tet40, teta, tetb, tetc, tetd, tete, tetg, teth, tetj, tetk, tetl, tetm, teto, tetpa, tetpb, tet, tetq, tets, tett, tetu, tetv, tetw, tetx, tety, tetz, tlrc, tmrb, tolc, tsnr, vana, vanb, vanc, vand, vane, yang, vanha, vanhb, vanhd, vanra, vanrb, vanrc, vanrd, vanre, vanrg, vansa, vansb, vansc, vansd, vanse, vansg, vant, vante, vantg, vanug, vanwb, vanwg, vanxa, vanxb, vanxd, vanxyc, vanxye, vanxyg, vanya, vanyb, vanyd, vanyg, vanz, vata, vatb, vatc, vatd, vate, vgaa, vgab, vgba, vgbb, vph, ykkc, ykkd or any combination thereof. The antibiotic gene can be any antibiotic resistance gene that is to be discovered or is as of yet undescribed.

In one embodiment, the query sequence of interest used to capture the relevant proximity junctions is any known microbial gene. For example, the query sequence of interest is an antibiotic resistance gene (e.g., any of the antibiotic resistance gene listed herein). Further to this embodiment, a sequence complementary to the query sequence of interest (e.g., an antibiotic resistance gene as provided herein) can be attached to or pre-loaded on a solid substrate (e.g., affinity beads or magnetic beads). The released proximity junctions can then be exposed to said solid substrate comprising the sequence complementary to the query sequence of interest under conditions conducive or permissive for hybridization. Following capture of the desired proximity junction(s), the one or more sequences present in the proximity junctions with the query sequence of interest (e.g., an antibiotic resistance gene as provided herein) can be labelled. The labeling can serve to allow detection of said one or more sequences upon binding of said labeled one or more sequences to a microarray comprising sequences complementary to the labeled one or more sequences. In some cases, the microarray comprises any antibiotic resistance gene known in the art and/or provided herein. Labeling of the one or more sequences can be performed using any method known in the art such as, for example, using PCR with one or more labeled nucleotides (e.g., Cy3 or Cy5 labeled dUTP). Detection of the binding of the labeled one or more sequences to sequence(s) on the microarray can be detected using any method known in the art.

Detection of Cancer Genes

In one embodiment, the methods provided herein are utilized to detect or determine the association or presence of one or more nucleic acids with a target nucleic acid (i.e., sequence of interest) in a sample obtained from a patient suffering from or suspected of having cancer. The one or more nucleic acids can be co-localized, adjacent to or in proximity to the target nucleic acid within a cell in the sample. The one or more nucleic acids can be any gene or gene mutation associated with the particular type of cancer. The target nucleic acid can be any gene or gene mutation associated with the particular type of cancer. The one or more nucleic acids and/or target nucleic acid can be any oncogene or mutant of a tumor suppressor gene known in the art that is or can be associated with the particular type of cancer. The sample can be a solid tumor sample (e.g., tissue biopsy) or a bodily fluid sample. The bodily fluid (also referred to as liquid biological sample or liquid biopsy) can be blood (including whole blood, leukocytes, peripheral blood mononuclear cells, buffy coat, plasma, and serum), sputum, tears, mucus, nasal washes, nasal aspirate, breath, urine, semen, ejaculate, saliva, meningeal fluid, amniotic fluid, glandular fluid, lymph fluid, nipple aspirate, bronchial aspirate, synovial fluid, joint aspirate, ascites, cells, a cellular extract, and cerebrospinal fluid. In some cases, the bodily fluid is blood. In some cases, the tumor sample is a formalin-fixed paraffin embedded (FFPE) tumor sample. In some cases, the tumor sample is a fresh-frozen sample.

Non-limiting examples of a cancer for use in the methods and compositions provided herein include adrenal cortical cancer, anal cancer, bile duct cancer, bladder cancer, bone cancer, brain or a nervous system cancer, breast cancer, cervical cancer, colon cancer, rectal cancer, colorectal cancer, endometrial cancer, esophageal cancer, Ewing family of tumor, eye cancer, gall-bladder cancer, gastrointestinal carcinoid cancer, gastrointestinal stromal cancer, Hodgkin Disease, intestinal cancer, Kaposi Sarcoma, kidney cancer, large intestine cancer, laryngeal cancer, hypopharyngeal cancer, laryngeal and hypopharyngeal cancer, leukemia, hairy cell leukemia (HCL), acute lymphocytic leukemia (ALL), acute myeloid leukemia (AML), chronic lymphocytic leukemia (CLL), chronic myeloid leukemia (CML), chronic myelomonocytic leukemia (CMML), non-HCL lymphoid malignancy (hairy cell variant, splenic marginal zone lymphoma (SMZL), splenic diffuse red pulp small B-cell lymphoma (SDRPSBCL), chronic lymphocytic leukemia (CLL), prolymphocytic leukemia, low grade lymphoma, systemic mastocytosis, or splenic lymphoma/leukemia unclassifiable (SLLU)), liver cancer, lung cancer, non-small cell lung cancer, small cell lung cancer, lung carcinoid tumor, lymphoma, lymphoma of the skin, malignant mesothelioma, multiple myeloma, nasal cavity cancer, paranasal sinus cancer, nasal cavity and paranasal sinus cancer, nasopharyngeal cancer, neuroblastoma, non-Hodgkin lymphoma, oral cavity cancer, oropharyngeal cancer, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma, adult soft tissue sarcoma, skin cancer, basal cell skin cancer, squamous cell skin cancer, basal and squamous cell skin cancer, melanoma, stomach cancer, small intestine cancer, testicular cancer, thymus cancer, thyroid cancer, uterine sarcoma, uterine cancer, vaginal cancer, vulvar cancer, Waldenstrom Macroglobulinemia, and Wilms Tumor.

In one embodiment, the query sequence of interest used to capture the relevant proximity junctions is any known oncogene, mutation of a tumor suppressor gene or a housekeeping gene. Further to this embodiment, a sequence complementary to the query sequence of interest (e.g., oncogene, mutation of a tumor suppressor gene or a housekeeping gene) can be attached to or pre-loaded on a solid substrate (e.g., affinity beads or magnetic beads). The released proximity junctions can then be exposed to said solid substrate comprising the sequence complementary to the query sequence of interest under conditions conducive or permissive for hybridization. Following capture of the desired proximity junction(s), the one or more sequences present in the proximity junctions with the query sequence of interest (e.g., oncogene, mutation of a tumor suppressor gene or a housekeeping gene) can be labelled. The labeling can serve to allow detection of said one or more sequences upon binding of said labeled one or more sequences to a microarray comprising sequences complementary to the labeled one or more sequences. In some cases, the microarray comprises any oncogene or mutation of a tumor suppressor gene known in the art and/or provided herein. Labeling of the one or more sequences can be performed using any method known in the art such as, for example, using PCR with one or more labeled nucleotides (e.g., Cy3 or Cy5 labeled dUTP). Detection of the binding of the labeled one or more sequences to sequence(s) on the microarray can be detected using any method known in the art.

EXAMPLES

The following example is given for the purpose of illustrating various embodiments of the disclosure and is not meant to limit the present disclosure in any fashion. Changes therein and other uses which are encompassed within the spirit of the disclosure, as defined by the scope of the claims, will be recognized by those skilled in the art.

Example 1: Use of Capture Hi-C Method on Mixed Cell Population: Proof of Principle Introduction This example demonstrates a proof of principle on the use of the capture Hi-C methods provided herein to enrich for Hi-C interactions for a specific target sequence in a mixed cell population.
Materials and Methods To test this method, a library of proximity junctions derived from a mixed population of microbial cells (i.e., *Bacillus subtilis*, and *Escherichia coli*) was generated using the methods provided herein and described in FIG. 1. In particular, a mixed population of intact *Bacillus subtilis*, and *Escherichia coli* cells were treated with a cross-linker (1% formaldehyde for 20 minutes at room temperature) and quenched with glycine at a final concentration of 1%. Subsequently, the cross-linked chromatin was purified from the mixed microbial cell population by a combination of physical (bead beating) and chemical (1% Triton X100 followed by 1% SDS; heated to 65° C.), followed by pelleting of cross-linked material and washing with tris-buffered saline. The DNA within the cross-linked chromatin was fragmented by restriction enzyme digest and overhanging ends filled in using the Klenow fragment of *E. coli* DNA polymerase I, incorporating a biotinylated deoxyadenosine in the process. The fragmented cross-linked chromatin was then subjected to proximity ligation using T4 DNA ligase for 4 hours at room temperature. The cross-links were reversed by treating with proteinase K and heating to 65° C. for 1 h. DNA was purified using column chromatography. Purified DNA containing an internal biotin was then captured using streptavidin coated paramagnetic beads. NGS sequencing adapters were added to the capture DNA sequences by tagmentation (i.e., transposon cleaving and tagging of the DNA) using Nextera enzyme. The beads were washed and then subjected to PCR to create an Illumina-compatible sequencing library (i.e., input Hi-C library).

Following PCR amplification of the input Hi-C library, excess primers were removed using solid phase reversible immobilization (SPRI) bead methods and quantitated by fluorometry. To facilitate selection of proximity junctions comprising a target sequence and detecting sequences associated therewith, capture probes predicted to hybridize to a region in each of these microbial species were generated (Table 1) and capture was performed independently for each of the probes.

TABLE 1

Capture Probes used in this example

| Target Probe Name | Description (i.e., target gene/ region) | Sequence (SEQ ID NO.) |
|---|---|---|
| *Bacillus subtilis* | Capture Probe | TGATTTTCCTCAAAATATGCTCAATCCAAAA TATACTTTTGATACTTTTGTCATCGGATCTG GAAACCGATTTGCACATGCTGCTTCCCTCGC AGTAGCGGAAGCGCCCGCGAAAGCTTACAAC CCTTTATTTATCTAT (SEQ ID NO. 1) |

TABLE 1-continued

Capture Probes used in this example

| Target Probe Name | Description (i.e., target gene/ region) | Sequence (SEQ ID NO.) |
|---|---|---|
| *Escherichia coli* | Capture Probe | TAATCTGCGGAGGCGTCAGTTTCCGCGCCTC ATGGATCAACTGCTGGGAATTGTCTAACAGC TCCGGCAGCGTATAGCGCGTGGTGGTCAACG GGCTTTGGTAATCAAGCGTTTTCGCAGGTGA AATAAGAATCAGCATA (SEQ ID NO. 2) |

More specifically, in separate reactions, 500 ng of the amplified, purified Hi-C input library was added to a capture hybridization reaction containing high salt buffer (6×SSC (0.9 M sodium chloride and 90 mM sodium citrate)) and one of the capture probes from Table 1. It should be noted that each capture probe is an oligonucleotide ranging from 120 to 150 nucleotides in length bearing a biotin molecule covalently bound to the 5' end of the oligonucleotide.

In each reaction, the probe and library were denatured together in the hybridization solution in a thermocycler heated to 95° C. After the 5 minute denaturation period, the probe was allowed to hybridize to the target sequence in the library at a temperature 5° C. below the predicted melting temperature ($T_m$) of the oligonucleotide capture probe. Following this period of hybridization, streptavidin-coated para-magnetic beads were added to the hybridization reaction, while maintaining the hybridization reaction at a temperature 5° C. below the $T_m$ of the capture probe. After 5 minutes of binding, the bead/hybridization reaction slurry was placed on a magnetic tube stand and the supernatant was removed. The beads were washed 3 times with heated 6×SSC and a single wash in a low salt buffer (1×SSC). The beads were resuspended in a PCR reaction and amplified as during the generation of the input Hi-C library. The input and capture library were then subjected to high throughput sequencing using an Illumina HiSeq 4000.

Results

In each case, sequences complementary to the probes were overrepresented in the capture library compared to other regions in the same genome (FIG. 2A). As expected, with this enrichment in reads corresponding to the captured sequence, an enrichment in the proportion of Hi-C signal associated with the captured sequence was observed (see FIG. 2B-D). The fraction of reads split in their mapping between two different regions of the host genome (FIG. 2B) and the fraction of read pairs mapping greater than 10 kb from each in the reference genome were increased (FIG. 2C), while the fraction of read pairs mapping a zero distance from each was decreased following capture (FIG. 2D). These metrics show that the capture Hi-C methods described are capable of enriching Hi-C interactions for a specific sequence.

Numbered Embodiments of the Disclosure

Other subject matter contemplated by the present disclosure is set out in the following numbered embodiments:

1. A method for determining a presence of one or more nucleic acids in a cell comprising a target nucleic acid, the method comprising:
generating proximity junctions between one or more nucleic acids and a target nucleic acid in a cell, wherein the cell is present in a sample comprising a mixed cell population;
capturing the proximity junctions between the one or more nucleic acids and the target nucleic acid, wherein the capturing comprises hybridizing the proximity junctions with an oligonucleotide comprising sequence complementary to the target nucleic acid; and
analyzing the one or more nucleic acids in the proximity junctions hybridized to the oligonucleotide comprising sequence complementary to the target nucleic acid, thereby determining the presence of the one or more nucleic acids in the cell comprising the target nucleic acid.

2. The method of embodiment 1, wherein the generation of the proximity junctions between one or more nucleic acids and the target nucleic acid comprises:
i.) incubating the sample comprising the cell with a cross-linking agent, wherein the cross-linking agent cross-links proteins and the one or more nucleic acids with the target nucleic acid in the cell, thereby generating a complex between the one or more nucleic acids and the target nucleic acid;
ii.) lysing the cell in a lysing buffer comprising a combination of one or more anionic detergents and one or more non-ionic detergents;
iii.) digesting the nucleic acid within the complex between the one or more nucleic acids and the target nucleic acid, thereby generating free nucleic acid ends;
iv.) ligating the digested nucleic acid; and
v.) releasing the one or more proximity junctions from the cross-linked protein, thereby generating the proximity junctions between the one or more nucleic acids and the target nucleic acid.

3. The method according to embodiment 2, wherein the cross-linking reagent comprises formaldehyde.

4. The method according to embodiment 2, further comprising the step of incubating the complex with a cross-linking quencher.

5. The method of embodiment 4, wherein the cross-linking quencher is glycine.

6. The method of any of embodiments 2-5, wherein the endonuclease is a restriction endonuclease.

7. The method of any of embodiments 2-5, wherein the endonuclease is DNase.

8. The method of any of embodiments 2-5, wherein the endonuclease is MNase.

9. The method of any of embodiments 2-8, wherein the releasing comprises reversing cross-linking by treating the cross-linked proteins with an agent selected from protease, heat or a combination thereof.

10. The method of any of embodiments 2-8, wherein the releasing comprises fragmenting the complex.

11. The method of any of the above embodiments, wherein the oligonucleotide comprising sequence complementary to the target nucleic acid further comprises a moiety attached to a 5' end.

12. The method of embodiment 11, wherein the moiety is biotin.

13. The method of any of the above embodiments, wherein the oligonucleotide comprising sequence complementary to the target nucleic acid is bound to a solid substrate.

14. The method of embodiment 13, wherein the solid substrate is selected from a bead, a well in a multi-well plate or surface of a slide.

15. The method of embodiment 14, wherein the bead is a magnetic bead.

16. The method of any of embodiments 2-15, further comprising labeling the free nucleic ends with biotin prior to step v.), whereby the proximity junctions generated following step v.) are biotin labeled.

17. The method of embodiment 16, wherein the proximity junctions that are biotin labeled are subjected to a purification step prior to capturing the proximity junctions, wherein the purification step comprises binding biotin with avidin or streptavidin attached to a solid substrate.

18. The method of any of the above embodiments, wherein the capturing further comprises enriching the target nucleic acid, wherein the enriching comprises performing polymerase chain reaction (PCR) by adding a set of primers and PCR reagents to the proximity junctions hybridized with the oligonucleotide comprising sequence complementary to the target nucleic acid, wherein each primer in the set of primers comprises sequence complementary to one or more additional target nucleic acids.

19. The method of any of embodiments 1-17, wherein the capturing further comprises enriching the target nucleic acid, wherein the enriching comprises performing PCR by adding a set of primers and PCR reagents to the proximity junctions hybridized with the oligonucleotide comprising sequence complementary to the target nucleic acid, wherein each primer in the set of primers comprises random sequence.

20. The method of embodiment 18 or 19, wherein the oligonucleotide and each primer in the set of primers further comprise adaptor sequences compatible with a next generation sequencing (NGS) system.

21. The method of embodiment 20, wherein the analyzing comprises sequencing the one or more nucleic acids in the proximity junctions.

22. The method of any of the above embodiments, wherein the analyzing comprises labeling the one or more nucleic acids present in the proximity junctions.

23. The method of embodiment 22, wherein the labeled one or more nucleic acids are hybridized to a microarray.

24. The method of any of the above embodiments, wherein the target nucleic acid is an antibiotic resistance gene.

25. The method of embodiment 24, wherein the sample comprising the mixed cell population is derived from the site of an infection in an individual.

26. The method of embodiment 24, wherein the sample comprising the mixed cell population is derived from an agricultural sample.

27. The method of embodiment 26, wherein the agricultural sample is cow rumen or manure.

28. The method of any of embodiments 24-27, wherein the target nucleic acid is present in a plasmid, virus or genomic DNA.

29. The method of any of embodiments 24-28, wherein each of the one or more nucleic acids is present in a plasmid, virus or genomic DNA.

30. The method of any of embodiments 1-23, wherein the target nucleic acid is an oncogene or a tumor suppressor gene.

31. The method of embodiment 30, wherein the sample comprising the mixed population is a tumor sample.

32. A method for detecting one or more nucleic acids associated with an antibiotic resistance gene comprising:
generating proximity junctions between one or more nucleic acids and an antibiotic resistance gene in a cell, wherein the cell is present in a sample comprising a mixed cell population;
capturing the proximity junctions between the one or more nucleic acids and the antibiotic resistance gene, wherein the capturing comprises hybridizing the proximity junctions with an oligonucleotide comprising sequence complementary to the antibiotic resistance gene; and
analyzing the one or more nucleic acids in the proximity junctions hybridized to the oligonucleotide comprising sequence complementary to the antibiotic resistance gene, thereby determining the presence of the one or more nucleic acids in the cell comprising the antibiotic resistance gene.

33. The method of embodiment 32, wherein the generation of the proximity junctions between one or more nucleic acids and the antibiotic resistance gene comprises:
i.) incubating the sample comprising the cell with a cross-linking agent, wherein the cross-linking agent cross-links proteins and the one or more nucleic acids with the antibiotic resistance gene in the cell, thereby generating a complex between the one or more nucleic acids and the antibiotic resistance gene;
ii.) lysing the cell in a lysing buffer comprising a combination of one or more anionic detergents and one or more non-ionic detergents;
iii.) digesting the nucleic acid within the complex between the one or more nucleic acids and the oncogene, thereby generating free nucleic acid ends;
iv.) ligating the digested nucleic acid; and
v.) releasing the one or more proximity junctions from the cross-linked protein, thereby generating the proximity junctions between the one or more nucleic acids and the antibiotic resistance gene.

34. The method according to embodiment 33, wherein the cross-linking reagent comprises formaldehyde.

35. The method according to embodiment 33, further comprising the step of incubating the complex with a cross-linking quencher.

36. The method of embodiment 35, wherein the cross-linking quencher is glycine.

37. The method of any of embodiments 33-36, wherein the endonuclease is a restriction endonuclease.

38. The method of any of embodiments 33-36, wherein the endonuclease is DNase.

39. The method of any of embodiments 33-36, wherein the endonuclease is MNase.

40. The method of any of embodiments 33-39, wherein the releasing comprises reversing cross-linking by treating the cross-linked proteins with an agent selected from protease, heat or a combination thereof.

41. The method of any of embodiments 33-39, wherein the releasing comprises fragmenting the complex.

42. The method of any of embodiments 32-41, wherein the oligonucleotide comprising sequence complementary to the antibiotic resistance gene further comprises a moiety attached to a 5' end.

43. The method of embodiment 42, wherein the moiety is biotin.

44. The method of embodiments 32-43, wherein the oligonucleotide comprising sequence complementary to the antibiotic resistance gene is bound to a solid substrate.

45. The method of embodiment 44, wherein the solid substrate is selected from a bead, a well in a multi-well plate or surface of a slide.

46. The method of embodiment 45, wherein the bead is a magnetic bead.

47. The method of any of embodiments 33-46, further comprising labeling the free nucleic ends with biotin prior to step v.), whereby the proximity junctions generated following step v.) are biotin labeled.

48. The method of embodiment 47, wherein the proximity junctions that are biotin labeled are subjected to a purification step prior to capturing the proximity junctions, wherein the purification step comprises binding biotin with avidin or streptavidin attached to a solid substrate.

49. The method of any of embodiments 32-48, wherein the capturing further comprises enriching the antibiotic resistance gene wherein the enriching comprises performing polymerase chain reaction (PCR) by adding a set of primers and PCR reagents to the proximity junctions hybridized with the oligonucleotide comprising sequence complementary to the antibiotic resistance gene, wherein each primer in the set of primers comprises sequence complementary to one or more additional target nucleic acids.

50. The method of any of embodiments 32-48, wherein the capturing further comprises enriching the antibiotic resistance gene, wherein the enriching comprises performing PCR by adding a set of primers and PCR reagents to the proximity junctions hybridized with the oligonucleotide comprising sequence complementary to the antibiotic resistance gene, wherein each primer in the set of primers comprises random sequence.

51. The method of embodiment 49 or 50, wherein the oligonucleotide and each primer in the set of primers further comprise adaptor sequences compatible with a next generation sequencing (NGS) system.

52. The method of embodiment 51, wherein the analyzing comprises sequencing the one or more nucleic acids in the proximity junctions.

53. The method of any of embodiments 32-52, wherein the analyzing comprises labeling the one or more nucleic acids present in the proximity junctions.

54. The method of embodiment 53, wherein the labeled one or more nucleic acids are hybridized to a microarray.

55. The method of any of embodiments 32-54, wherein the antibiotic resistance gene is present in a plasmid or the genome of the cell.

56. The method of any of embodiments 32-55, wherein each of the one or more nucleic acids is present in a plasmid or the genome of the cell.

57. The method of any of embodiments 32-56, wherein the sample is derived from the site of an infection in an individual.

58. The method of any of embodiments 32-56, wherein the sample is derived from an agricultural sample.

59. The method of embodiment 58, wherein the agricultural sample is cow rumen or manure.

60. A method for detecting one or more nucleic acids associated with an oncogene or a tumor suppressor gene comprising:
generating proximity junctions between one or more nucleic acids and an oncogene or tumor suppressor gene in a cell, wherein the cell is present in a sample comprising a mixed cell population derived from an individual;
capturing the proximity junctions between the one or more nucleic acids and the oncogene or the tumor suppressor gene, wherein the capturing comprises hybridizing the proximity junctions with an oligonucleotide comprising sequence complementary to the oncogene or the tumor suppressor gene; and
analyzing the one or more nucleic acids in the proximity junctions hybridized to the oligonucleotide comprising sequence complementary to the oncogene or the tumor suppressor gene, thereby determining the presence of the one or more nucleic acids in the cell comprising the oncogene or the tumor suppressor gene.

61. The method of embodiment 60, wherein the generation of the proximity junctions between one or more nucleic acids and the oncogene or the tumor suppressor gene comprises:
i.) incubating the sample with a cross-linking agent, wherein the cross-linking agent cross-links proteins and the one or more nucleic acids and the oncogene or the tumor suppressor gene in the cell, thereby generating a complex between the one or more nucleic acids and the oncogene or the tumor suppressor gene;
ii.) lysing the cell in a lysing buffer comprising a combination of one or more anionic detergents and one or more non-ionic detergents;
iii.) digesting the nucleic acid within the complex between the one or more nucleic acids and the oncogene or the tumor suppressor gene, thereby generating free nucleic acid ends;
iv.) ligating the digested nucleic acid; and
v.) releasing the one or more proximity junctions from the cross-linked protein, thereby generating the proximity junctions between the one or more nucleic acids and the oncogene or the tumor suppressor gene.

62. The method according to embodiment 61, wherein the cross-linking reagent comprises formaldehyde.

63. The method according to embodiment 61, further comprising the step of incubating the complex with a cross-linking quencher.

64. The method of embodiment 63, wherein the cross-linking quencher is glycine.

65. The method of any of embodiments 61-64, wherein the endonuclease is a restriction endonuclease.

66. The method of any of embodiments 61-64, wherein the endonuclease is DNase. 67. The method of any of embodiments 61-64, wherein the endonuclease is MNase.

68. The method of any of embodiments 61-67, wherein the releasing comprises reversing cross-linking by treating the cross-linked proteins with an agent selected from protease or heat.

69. The method of any of embodiments 61-67, wherein the releasing comprises fragmenting the complex.

70. The method of any of embodiments 60-69, wherein the oligonucleotide comprising sequence complementary to the antibiotic resistance gene further comprises a moiety attached to a 5' end.

71. The method of embodiment 70, wherein the moiety is biotin.

72. The method of embodiments 60-71, wherein the oligonucleotide comprising sequence complementary to the oncogene or the tumor suppressor gene is bound to a solid substrate.

73. The method of embodiment 72, wherein the solid substrate is selected from a bead, a well in a multi-well plate or surface of a slide.

74. The method of embodiment 73, wherein the bead is a magnetic bead.

75. The method of any of embodiments 61-74, further comprising labeling the free nucleic ends with biotin prior to step v.), whereby the proximity junctions generated following step v.) are biotin labeled.

76. The method of embodiment 75, wherein the proximity junctions that are biotin labeled are subjected to a purification step prior to capturing the proximity junctions, wherein the purification step comprises binding biotin with avidin or streptavidin attached to a solid substrate.

77. The method of any of embodiments 60-76, wherein the capturing further comprises enriching the oncogene wherein the enriching comprises performing polymerase chain reaction (PCR) by adding a set of primers and PCR reagents to the proximity junctions hybridized with the oligonucleotide comprising sequence complementary to the oncogene, wherein each primer in the set of primers comprises sequence complementary to one or more additional target nucleic acids.

78. The method of any of embodiments 60-76, wherein the capturing further comprises enriching the oncogene or the tumor suppressor gene, wherein the enriching comprises performing PCR by adding a set of primers and PCR reagents to the proximity junctions hybridized with the oligonucleotide comprising sequence complementary to the oncogene or the tumor suppressor gene, wherein each primer in the set of primers comprises random sequence.

79. The method of embodiment 77 or 78, wherein the oligonucleotide and each primer in the set of primers further comprise adaptor sequences compatible with a next generation sequencing (NGS) system.

80. The method of embodiment 79, wherein the analyzing comprises sequencing the one or more nucleic acids in the proximity junctions.

81. The method of any of embodiments 60-80, wherein the analyzing comprises labeling the one or more nucleic acids present in the proximity junctions.

82. The method of embodiment 81, wherein the labeled one or more nucleic acids are hybridized to a microarray.

83. The method of any of embodiments 60-82, wherein the sample comprising the mixed population is a tumor sample.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of detecting one or more nucleic acids in a microbial cell comprising a target nucleic acid, the method comprising:

generating proximity junctions comprising one or more microbial genes and a target nucleic acid within a microbial cell present in a sample comprising a mixed cell population comprising microbial cells, wherein either the target nucleic acid, the one or more microbial genes or both are extra-chromosomal;

hybridizing the proximity junctions comprising the one or more microbial genes and the target nucleic acid with an oligonucleotide comprising sequence complementary to the target nucleic acid, wherein the target nucleic acid is a known microbial gene; and extending the oligonucleotide comprising sequence complementary to the target nucleic acid from the previous step in a primer extension reaction to generate primer extension products comprising sequence from the one or more microbial genes, thereby detecting the one or more microbial genes in the proximity junctions hybridized to the oligonucleotide comprising sequence complementary to the target nucleic acid.

2. The method of claim 1, wherein the generation of the proximity junctions comprising one or more microbial genes and the target nucleic acid comprises:

(i) incubating the sample comprising the mixed cell population with a cross-linking agent, wherein the cross-linking agent cross-links proteins to the one or more microbial genes and the target nucleic acid within the microbial cell, thereby generating a complex comprising the proteins, the one or more microbial genes and the target nucleic acid within the microbial cell;

(ii) lysing the microbial cell in a lysing buffer comprising a combination of one or more anionic detergents and one or more non-ionic detergents;

(iii) digesting the nucleic acid within the complex comprising the one or more microbial genes and the target nucleic acid, thereby generating free nucleic acid ends;

(iv) ligating the digested nucleic acid; and (v) releasing the one or more proximity junctions from the cross-linked proteins, thereby generating the proximity junctions comprising the one or more microbial genes and the target nucleic acid.

3. The method according to claim 2, further comprising the step of incubating the complex with a cross-linking quencher.

4. The method of claim 2, wherein the releasing comprises reversing cross-linking by treating the cross-linked proteins with an agent selected from protease, heat or a combination thereof.

5. The method of claim 2, wherein the releasing comprises fragmenting the complex.

6. The method of claim 1, wherein the oligonucleotide comprising sequence complementary to the target nucleic acid further comprises a moiety attached to a 5' end.

7. The method of claim 1, wherein the oligonucleotide comprising sequence complementary to the target nucleic acid is bound to a solid substrate.

8. The method of claim 2, further comprising labeling the free nucleic ends with biotin prior to step (iv), whereby the proximity junctions generated following step (v) are biotin labeled.

9. The method of claim 8, wherein the proximity junctions that are biotin labeled are subjected to a purification step prior to capturing the proximity junctions, wherein the purification step comprises binding biotin with avidin or streptavidin attached to a solid substrate.

10. The method of claim 1, wherein the primer extension comprises performing polymerase chain reaction (PCR) using the oligonucleotide comprising sequence complementary to the target nucleic acid and at least one primer from a set of primers added along with PCR reagents to the proximity junctions hybridized with the oligonucleotide comprising sequence complementary to the target nucleic acid, wherein the set of primers is a mixed pool of primers such that each primer in the set of primers comprises sequence complementary to a known sequence that may or may not be present in the one or more microbial genes in the proximity junctions.

11. The method of claim 1, wherein the primer extension comprises performing PCR using the oligonucleotide comprising sequence complementary to the target nucleic acid and at least one primer from a set of primers added along with PCR reagents to the proximity junctions hybridized with the oligonucleotide comprising sequence complementary to the target nucleic acid, wherein each primer in the set of primers comprises random sequence.

12. The method of claim 10, wherein the oligonucleotide and each primer in the set of primers further comprise adaptor sequences compatible with a next generation sequencing (NGS) system.

13. The method of claim 12, further comprising the steps of generating a sequencing library using the adaptor sequences and sequencing the one or more microbial genes in the proximity junctions following the detecting step.

14. The method of claim 11, wherein the oligonucleotide and each primer in the set of primers further comprise adaptor sequences compatible with a next generation sequencing (NGS) system.

15. The method of claim 14, further comprising the steps of generating a sequencing library using the adaptor sequences and sequencing the one or more microbial genes in the proximity junctions following the detecting step.

16. The method of claim 1, wherein the primer extension is performed using labeled nucleotides, thereby generating labeled primer extension products comprising sequence complementary to the one or more microbial genes.

17. The method of claim 16, further comprising hybridizing the labeled primer extension products to a microarray.

18. The method of claim 1, wherein the sample comprising the mixed cell population comprising microbial cells is derived from the site of an infection in an individual.

19. The method of claim 1, wherein the sample comprising the mixed cell population comprising microbial cells is derived from an agricultural sample.

20. The method of claim 19, wherein the agricultural sample is cow rumen or cow manure.

21. The method of claim 1, wherein the target nucleic acid or each of the one or more microbial genes is present in a plasmid, virus or genomic DNA.

22. The method of claim 1, wherein the one or more microbial genes or the known microbial gene are selected from the group consisting of an endogenous microbial gene, a toxic microbial gene and an antibiotic resistance gene.

23. The method of claim 1, wherein the microbial cells in the mixed cell population are bacterial cells.

* * * * *